United States Patent [19]

Thompson

[11] 3,955,931

[45] May 11, 1976

[54] OXYGEN GENERATOR

[75] Inventor: Tommy Lewis Thompson, Melbourne, Fla.

[73] Assignee: Life Support, Inc., Melbourne, Fla.

[22] Filed: Feb. 19, 1974

[21] Appl. No.: 443,238

[52] U.S. Cl. ................................ 23/281; 128/142.3; 128/203

[51] Int. Cl.[2] ................ A61M 15/00; A61M 16/00; A62B 7/08; B01J 7/00

[58] Field of Search .............. 23/281, 282; 128/142, 128/142.3, 141 R, 203

[56] References Cited

UNITED STATES PATENTS

| | | | |
|---|---|---|---|
| 2,392,199 | 1/1946 | Steiger | 23/282 |
| 2,558,756 | 7/1951 | Jackson et al. | 23/281 |
| 3,536,070 | 10/1970 | Bovard | 128/142.3 |
| 3,580,250 | 5/1971 | Oroza | 23/281 |
| 3,620,683 | 11/1971 | Hwoschwsky et al. | 23/281 |
| 3,736,104 | 5/1973 | Churchill et al. | 23/281 |
| 3,737,287 | 6/1973 | Churchill et al. | 128/203 |
| 3,742,683 | 7/1973 | Sebest et al. | 23/281 UX |
| 3,767,366 | 10/1973 | Staub | 23/281 |

*Primary Examiner*—Joseph Scovronek
*Assistant Examiner*—Bradley R. Garris
*Attorney, Agent, or Firm*—Hill, Gross, Simpson, Van Santen, Steadman, Chiara & Simpson

[57] ABSTRACT

Exothermic reacting chemical oxygen generators are heat insulated with a hydrate to protect the user. The hydrate, when heated by the generator releases water which is vaporized and allowed to escape to a zone which will not be grasped by the user or is absorbed in a surrounding inert insulation layer where it can condense and revaporize as the heat wave passes through the surrounding inert insulation. The generator is preferably in the form of a disposable canister such as a tin can containing an oxygen generating chlorate candle and means for igniting the candle. A mask or cannula carrying cap is snapped on the can and has mechanism for piercing the can and activating the ignition means to flow oxygen to the mask or cannula.

The preferred insulation includes a hydrate salt layer sandwiched between metal foil-backed refractory fiber blankets and covered with a sleeve.

9 Claims, 6 Drawing Figures

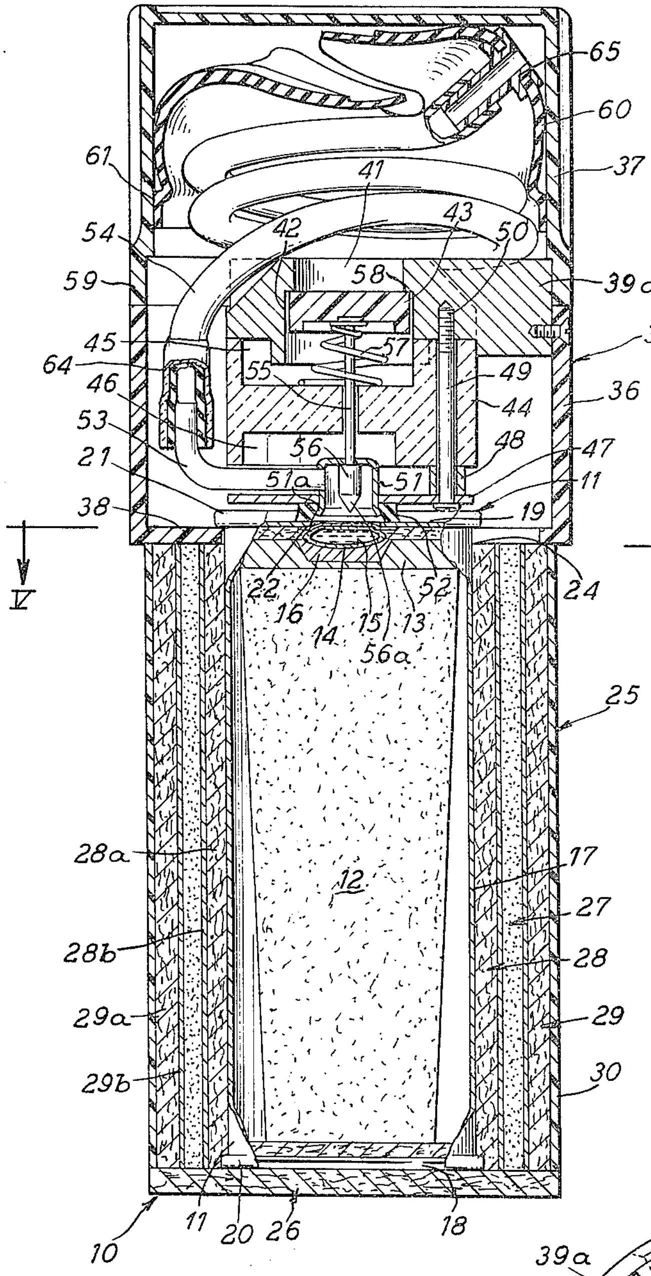
Fig. 2
Fig. 2A
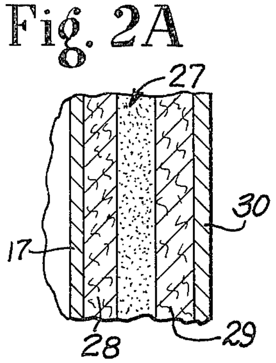
Fig. 4
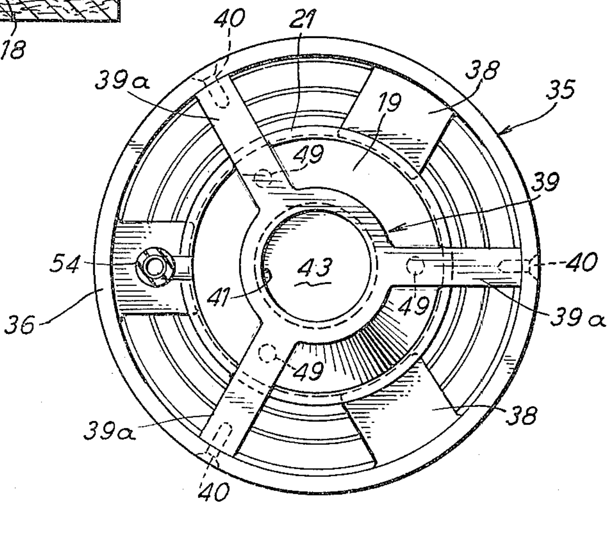

OXYGEN GENERATOR

BACKGROUND OF THE INVENTION

1. Field of the Invention

This invention relates to the art of protecting the users of exothermic reacting chemical oxygen generators from heat released by the generators and specifically deals with a disposable tin can type chlorate candle oxygen generator with a snap-on cap having mechanism for activating the candle and delivering the oxygen to a cap carried face mask where the body of the can is insulated with a hydrate salt layer sandwiched between refractory fiber insulation layers so that the can can be handled without discomfort from heat released during the oxygen generating decomposition of the chlorate candle.

In my prior U.S. Pat. Nos. 3,702,305 and 3,725,156 there are disclosed and claimed chemical formulations and ignition cone compositions adapted for oxygen generator cells disclosed and claimed in the Churchill and Thompson U.S. Pat. No. 3,736,104. These compositions and generator cells can be used with the present invention to avoid heretofore required oxygen dispensing and cell carrying cases described and claimed in the Churchill, Thompson, and McBride U.S. Pat. No. 3,733,008.

2. Prior Art

The Jackson and Bovard U.S. Pat. No. 2,558,756 seeks to insulate an oxygen generating composition in a canister with an envelope of potassium perchlorate between the composition and canister which is alleged to decompose endothermically with evolution of oxygen under the heat of reaction of the composition in the canister. The patentees contend that such an envelope of potassium perchlorate plus glass wool surrounding the envelope in the canister will hold the external temperature of the canister to a maximum of about 200° C. (392° F.). Such high temperatures do not permit the canister to be grasped by the user and, therefore, Jackson and Bovard were forced to mount the canister in an envelope providing an air space around the canister and formed of a relatively non-heat-conducting material such as a laminated fabric resin equipped with perforations for radiating heat. Since potassium perchlorate has a low heat conductivity and a very low heat of decomposition into the chloride and oxygen, it would appear that these characteristics of the perchlorate are the reason for the insulating action and not, as stated in the patent, by an endothermic decomposition.

SUMMARY OF THIS INVENTION

This invention now provides chemical oxygen generator canisters housing a combustible material which upon ignition undergoes exothermic reaction to evolve oxygen which are insulated so efficiently that they may be grasped without discomfort even when the composition reaches its highest temperature in generating the oxygen. The canisters of this invention are insulated with a hydrate salt that releases its water when heated by temperatures developed during the exothermic decomposition of the oxygen generating material in the canister. The released water is vaporized thereby converting sensible heat into heat of vaporization and the vapor is allowed to escape to a zone of the canister which is not grasped by the user or is condensed in a surrounding insulating layer and then reevaporated as the heat wave passes through this outer insulating layer.

Useful hydrate salts are inexpensive and are preferably sandwiched between aluminum foil backed layers of inert refractory fibers. Surface temperatures of about 160° F. can be maintained.

The preferred hydrate salts contain a large percentage of hydrated water and break down at a reasonably low temperatures, for example, less than 200° C.

Epsom salt ($MgSO_4 \cdot \mathbf{7H_2O}$), trisodium phosphate ($Na_3PO_4 \cdot \mathbf{12H_2O}$), and glauber's salt ($Na_2SO_4 \cdot \mathbf{10H_2O}$) are preferred insulating hydrate salts but the following hydrate salts are also useful.

| | |
|---|---|
| $Al_2(SO_4)_3 \cdot 18H_2O$ | $Na_2SO_3 \cdot 7H_2O$ |
| $NH_4Al(SO_4)_2 \cdot 12H_2O$ | $SrCl_2 \cdot 6H_2O$ |
| $(NH_4)\ Cr(SO_4)_2 \cdot 12H_2O$ | $Sr(OH)_2 \cdot 8H_2O$ |
| $BaO_2 \cdot 8H_2O$ | $ZnF_2 \cdot 4H_2O$ |
| $Cr_2(SO_4)_3 \cdot 18H_2O$ | $Zn(NO_3)_2 \cdot 6H_2O$ |
| $CoCl_2 \cdot 6H_2O$ | $ZrOCl_2 \cdot 8H_2O$ |
| $Fe(SO_4) \cdot 7H_2O$ | $CaCl_2 \cdot 6H_2O$ |
| $Mg_3(PO_4)_2 \cdot 22H_2O$ | $CoBr_2 \cdot 6H_2O$ |
| $NiSO_4 \cdot 7H_2O$ | $CuSO_4 \cdot 5H_2O$ |
| $KAl(SO_4) \cdot 12H_2O$ | $Fe_2(SO_4)_3 \cdot 9H_2O$ |
| $K[Cr(SO_4)_2]\ 12H_2O$ | $Mg(H_2PO_2)_2 \cdot 6H_2O$ |
| $KMgPO_4 \cdot 6H_2O$ | $MgSO_4 \cdot 7H_2O$ |
| $KNaCO_3 \cdot 6H_2O$ | $MgSO_3 \cdot 6H_2O$ |
| $K_2PO_3 \cdot 4H_2O$ | $MnCl_2 \cdot 4H_2O$ |
| $RbFe(SeO_4)_2 \cdot 12H_2O$ | $NdCl_3 \cdot 6H_2O$ |
| $Na_2B_4O_7 \cdot 10H_2O$ | $Na_3PO_4 \cdot 12H_2O$ |
| $Na_3Li(SO_4)_2 \cdot 6H_2O$ | $NiSO_4 \cdot 6H_2O$ |
| $Na_2H_2P_2O_6 \cdot 6H_2O$ | $Na_2HPO_4 \cdot 12H_2O$ |
| $NaSiO_3 \cdot 9H_2O$ | $Na_2SO_4 \cdot 10H_2O$ |

Oxygen generator canisters of the type disclosed and claimed in the aforesaid U.S. Pat. No. 3,736,104 housing the sodium chlorate-sodium oxide composition of my aforesaid U.S. Pat. No. 3,702,305 and when ignited with ignition cone material of my aforesaid U.S. Pat. No. 3,725,156 and sized to produce an average of about 5.5 liters per minute of medically pure oxygen for 15 minutes reach surface temperatures of around 460° F. which, of course, is far too hot to handle with bare hands. Insulation of these canisters with bulky one-half inch thick blankets of refractory fibrous materials of the best known efficiency only reduce the outer surface temperature of these canisters to 310° F. which is still too hot to handle with bare hands. By placing a layer of a hydrate salt such as Epsom salt within the insulation according to this invention, the maximum outer surface temperature of the canisters was reduced to 160° F. which can be comfortably handled. It is pointed out that the apparent surface temperature of an object to a person touching it depends on the thermal conductivity of the surface and, therefore, a metal surface of 130° F. will feel warmer than an insulated surface of 160° F. Therefore, while 160° F. would normally sound high for handling with bare hands, the canisters of this invention can be comfortably grasped especially where the outer surface is composed of an insulating material.

The mechanism of heat absorption according to this invention is apparently the decomposition of the hydrate as indicated by the following formula:

Epsom salt $$MgSO_4 \cdot 7H_2O \xrightarrow{150\text{–}200^\circ\ C.} MgSO_4 + 7H_2O\ (g) \quad \Delta H_r = 98.6\ \text{K Cal/mole}$$

which can absorb 400 cal/(gm of $MgSO_4 \cdot \mathbf{7H_2O}$).

Tri sodium phosphate $$Na_3PO_4 . 12H_2O \xrightarrow{100° C.} Na_3PO_4 + 12H_2O(g) \quad \Delta H_r = 155.4 \text{ K Cal/mole}$$

which can absorb 408.8 cal/ (gm of $Na_3PO_4$ . $12H_2O$)

Glauber's salt $$Na_2SO_4 . 10H_2O \xrightarrow{100° C.} Na_2SO_4 + 10H_2O\ (g) \quad \Delta H_r = 124.58 \text{ K Cal/mole}$$

which can absorb 386.7 cal/ (gm $Na_2SO_4$ . $10H_2O$).

The heat is actually used to break down the hydrate and vaporize the water of hydration so the heat is not really absorbed but is converted from sensible heat to the heat of vaporization for the water. Where the hydrate salt is sandwiched between two layers of aluminum foil backed refractory fibrous material blankets, water can sometimes be observed escaping from the top of the inner aluminum foil barrier. If the foil is omitted the hydrate breaks down and vapor escapes radially and axially through the insulation, the process appearing to be one of hydrate break-down with condensation of moisture in the outer layer of insulation. As the "heat wave" penetrates the insulation, the water is reevaporated until it escapes from the outermost surface of the insulation. The canister can be handled comfortably but the insulation may become damp.

Glauber's salt has the disadvantage of being efflorescent so canisters equipped with this insulation material should be sealed in a moisture-proof envelope before use.

It is then an object of this invention to provide a heat insulator including a layer of a hydrate salt.

Another object of this invention is to provide oxygen generator canisters of a combustion material which, when ignited, undergoes exothermic reaction with evolution of oxygen, which canisters are heat insulated by a layer of a salt which releases water at temperatures generated by the composition and convert sensible heat into heat of vaporization so that the canisters can be grasped by bare hands without discomfort.

Another object of this invention is to provide an oxygen generator canister with an envelope of insulating material including a layer of hydrate salt sandwiched between aluminum foil-backed refractory fiber material.

A still further object of the invention is to provide a chlorate candle oxygen generator in the form of a disposable tin can with one end thereof having an oxygen dispensing orifice with a puncturable seal and a surrounding bead receiving a snap-on cap with mechanism for piercing the seal and activating the chlorate candle to dispense oxygen through a tube to a face mask carried by the cap and with the side wall of the can covered by a multi-layer envelope of insulating material including an inner layer of a hydrate salt enabling the can to be comfortably grasped even when the tin can reaches its highest temperature during oxygen generation.

A still further object of the invention is to provide a disposable oxygen generator insulated canister with a snap-on activating and dispensing cap.

A specific object of this invention is to eliminate heretofore required carriers and envelopes for oxygen generators which release heat and to so insulate the generator that it can be comfortably grasped with bare hands during oxygen generation.

Other and further objects of this invention will be apparent to those skilled in this art from the following detailed description of the annexed sheets of drawings which by way of a preferred example only, illustrate one embodiment of the invention.

A BRIEF DESCRIPTION OF THE DRAWINGS

FIG. 2 is a vertical cross sectional view along the line II—II of FIG. 1 and also including a vertical cross section of an actuator and dispensing cap snapped on the top of the canister;

FIG. 2-A is a fragmentary vertical sectional view of the generator of FIG. 2 with the foil backings of the blankets removed according to this invention.

Figure 5:
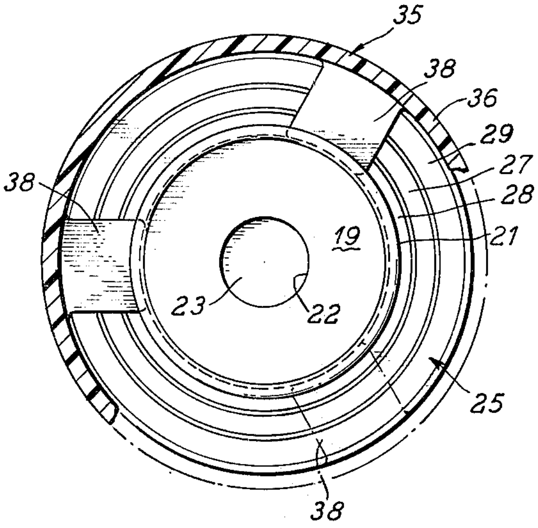
Figure 3:
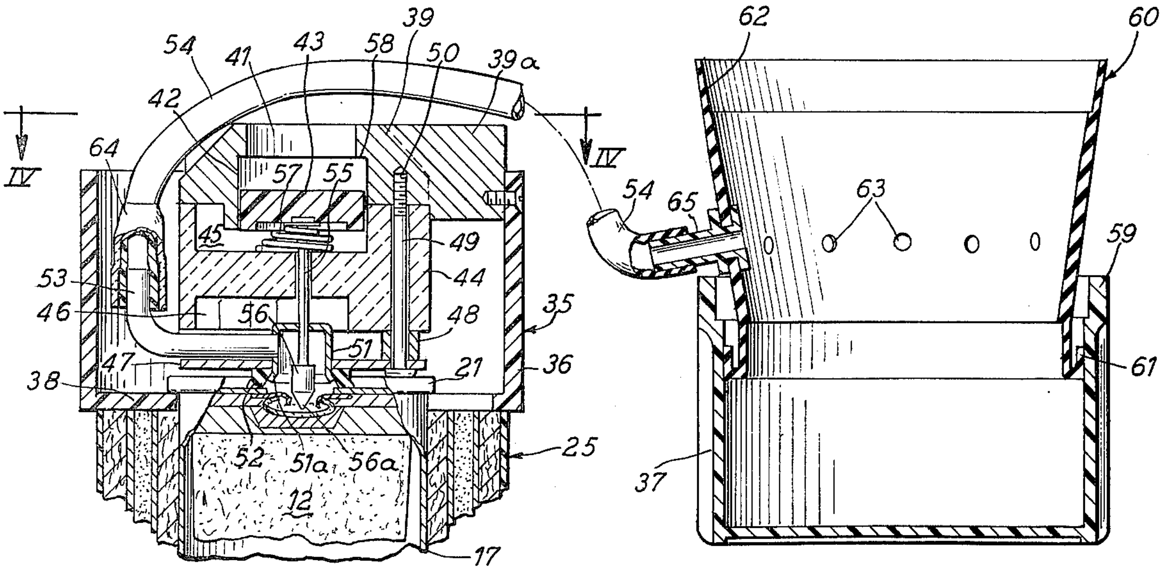

FIG. 3 is a fragmentary view similar to FIG. 2 but showing the canister and cap in oxygen dispensing position;

FIG. 4 is a plan view of the cap taken along the line IV—IV of FIG. 3; and FIG. 5 is a cross section view of the cap taken along the line V—V of FIG. 2.

A BRIEF DESCRIPTION OF THE PREFERRED EMBODIMENT

Figure 1:
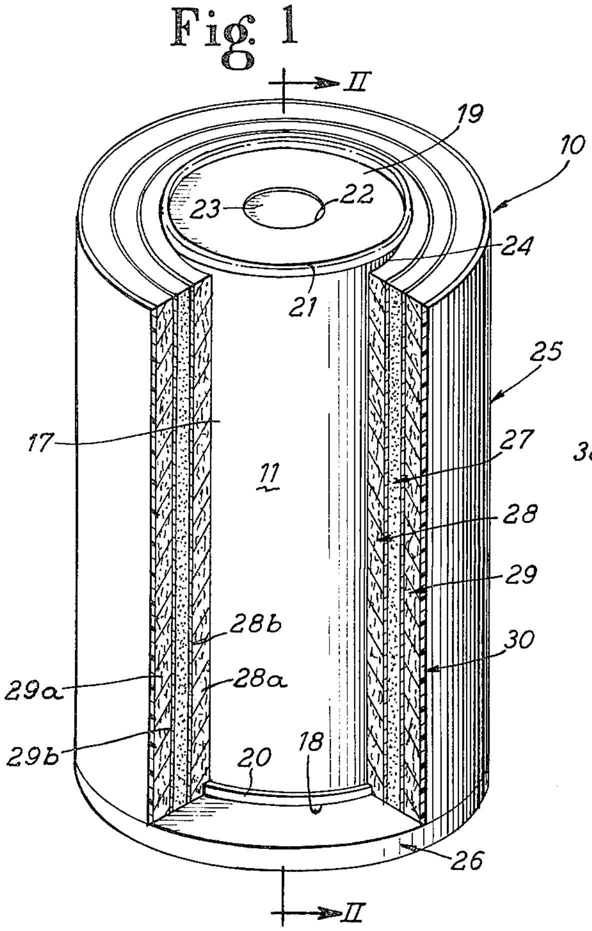
FIG. 1 is a perspective view, with parts broken away and shown in vertical cross section, of an insulated oxygen generator canister according to this invention.

As shown in FIGS. 1 and 2, the oxygen generator 10 includes a tin plated steel can 11, hereinafter referred to as a tin can, providing a casing for a compacted sodium chlorate candle 12 having the composition of my aforesaid U.S. Pat. No. 3,702,305 which is covered with an ignition cone composition 13 disclosed and claimed in my aforesaid U.S. Pat. No. 3,725,156. A glass vial 14 filled with water 15 rests on or is embedded in the ignition cone 13. If desired, a first fire composition 16 can surround the vial 14 and have the following formula:

| | |
|---|---|
| $NaClO_3$ | 18% by weight |
| $NaIO_3$ | 38% by weight |
| $Na_2O$ | 44% by weight. |

The tin can 11 has the conventional cylindrical side wall 17 with flat bottom and top end walls 18 and 19 connected and sealed to the side wall by beads 20 and 21, respectively. The bottom wall 18 is imperforate but the top wall 19 has a central circular orifice 22 closed by a puncturable metal foil seal 23 secured either to the top or bottom face of the end wall 19.

The cylindrical wall 17 of the tin can 11 is covered to a level 24 just below the bead 21 by insulation 25 and the bottom wall 18 is covered by insulation 26. The top wall or end 19 and the bead 21 remain uncovered.

In accordance with this invention the insulation 25 includes a layer of a hydrate salt 27 sandwiched between aluminum foil-backed refractory fiber blankets 28 and 29 with a cardboard, plastics material or metal sleeve 30 surrounding the outer blanket 29. If the aluminum foil around the hydrate layer is omitted as shown in FIG. 2-A, the outer sleeve 30 should be porous to allow water vapor to escape through the periphery in a radial direction as well as through the ends in an axial direction. As shown, the blanket 28 has a relatively thick layer 28*a* composed of refractory fibrous material surrounding the cylindrical side wall 17 of the tin can and backed by a backing layer of thin aluminum foil 28*b*. The blanket 29 has a relatively thick outer layer 29*a* of refractory fibrous material on a backing 29*b* of the aluminum foil. The outer fibrous layer 29*a* is covered by the sleeve 30. Thus, the hydrate salt 27 is sandwiched between the aluminum foil backings 28*b* and 29*b* of the refractory fibrous blankets 28 and 29.

The blankets 28 and 29 are preferably composed of a product sold under the trademark "Fiberfrax" by the Carborundum Company of Niagara Falls, New York where the fibers have approximately the following chemical analysis in percent by weight:

| | |
|---|---|
| $Al_2O_3$ | 50.9 percent |
| $SiO_2$ | 46.8 percent |
| $B_2O_3$ | 1.2 percent |
| $Na_2O$ | 0.8 percent |
| Trace Inorganics | 0.3–0.5 percent. |

Other suitable insulating blankets include "Foamglas" (sold by Pittsburgh Corning Corp., Pittsburgh, Pa.) and "Ceramic Foam" (sold by Dow Chemical Co., Midland, Mich.). These materials have an advantage of being non-porous and can be used without the aluminum foil.

The aluminum foil backing is about 0.002 inches thick and the thickness of each blanket is about one-quarter inch.

The layer of hydrate salt 27 may vary in thickness to provide the desired insulating effect. When one quarter inch Fiberfrax blankets are used, the layer 27 need only be about one quarter of an inch but it should be understood that the thickness of the blankets and the hydrate salt layer can be varied to suit use conditions of the generator.

The bottom blanket 26 covering the bottom end wall of the tin can may be as thick as desired and also covers the ends of the insulation layers 27–29. Since the blanket 26 is porous, it will be noted that the bottom end of the insultion layer 27 is vented through the porous blanket to the atmosphere.

It will also be noted that the top end of the insulation layer 27 is vented to the atmosphere and as will be more fully hereinafter explained, the cap which is snapped on the top of the can to activate the chlorate candle 12 and dispense oxygen to a face mask will not block the open top venting of this layer.

The following calculations illustrate the superiority of the insulation of this invention as compared with ordinary insulation. For illustrative purposes high temperature reacting chlorate candles containing iron fibers, barium peroxide and glass fibers in a tin plated steel can were used.

EXAMPLE I — BARE CANISTER, NO INSULATION

Canister details:
tin plated steel
emissivity = 0.60 (tin oxide)
diameter = 2 inches
length = 4.5 inches
Candle details:
Average flow rate — 4 LPM
Duration of flow = 15 minutes Fe = 2.3% $BaO_2$ = 4%, Glass Fibers = 6%, sodium chlorate balance
Length = 3.1, heat output = 154.1 BTU
Calculation of surface temperature:
Neglecting heat storage within the canister and unsteady state conditions, the surface temperature can be calculated from the expression:

$$q = (h_c + h_r)\, A_o\, \Delta t \qquad (4)$$

where
q = Rate of heat transfer, BTU/hr.
$(h_c + h_r)$ = combined heat transfer coefficient for natural correction plus radiation, BTU/(sq. ft.) (hr.) (°F.)
$A_o$ = the surface area, sq. ft.
$\Delta t$ = the difference in temperature between the canister and its surroundings, °F.

For purposes of calculation:

$$h_c = 0.27\, (\Delta t\, /D_o)^{0.25} \qquad (5)$$

where
$D_o$ is the diameter, ft.

$$h_r = 4\, \epsilon\sigma\, T_{avg} \qquad (6)$$

where
$\epsilon$ is the emissivity;
$\sigma$ is the stefan-Boltzmann constant, BTU/ (sq. ft.) ($h_r$) (°R)$^4$; and
$T_{avg}$ is the average of the canister temperature and that of its surroundings, °R.

With the appropriate substitutions, equation (4) becomes:

$$(154.1/0.25) = (h_c + h_r)\, (0.24)\, (t - 75) \qquad (7)$$

The canister surface temperature from this equation is 659° F.

EXAMPLE II — INSULATED CANISTER

The canister details, dimensions, heat output, etc. are the same as in Example I, with a thickness of ½ inch of mineral wool insulation surrounding the tin can
$k$ = 0.024 BTU/ (ft.) (hr.) (°F.) over the canister and $\epsilon$ = 1 at its outer surface, equation (4) becomes $$(154.1/0.25) = (h_c + h_r)\, (0.46)\, (t - 75) \qquad (8)$$

and the outer surface temperature of the insulation is 411° F.

There is another disadvantage to a simply insulated canister; when the canister temperature is increased the reaction rate is accelerated. Heat flow through the insulation on the canister is given by:

$$q = \frac{kA_m\, \Delta t}{x} \qquad (9)$$

where $A_m$ = the mean area of insulation, sq. ft., $\Delta t$ is the temperature change across the insulation, °F., $x$ is the thickness of insulation, ft., and $k$ is the thermal conductivity of the insulation BTU/ (ft.) (hr.) (°F). Solution of this equation for the canister wall temperature gives a value in excess of 3,000° F. Hence the reaction rate must be increased. In practice the insulation would probably melt and the tin plate ignite.

EXAMPLE III — INSULATION PLUS HEAT ABSORBENT

In this case the canister is covered by a layer of mineral wool 0.05 in thickness, or the equivalent amount of some other material with the same value of $(k/x)$. This is followed by a layer of $Na_3PO_4 \cdot 12H_2O$ approximately 0.2 in. thick, depending on its bulk density. The trisodium phosphate is sandwiched between two layers of aluminum foil. A final layer of mineral wool ¼ inch thick covers the outer surface.

The hydrate decomposes at 100° C. (212° F.). To calculate the outer surface temperature it is necessary to equate the heat flow through the outer thickness of insulation to that transferred to the surroundings, as:

$$q = \frac{kA_m}{x}(212 - t) = (h_c + h_r)\,A_o\,(t - 75) \qquad (10)$$

or $$\frac{(0.024)(0.40)(212 - t)}{(0.25/12)} = (h_c + h_r)(0.46)(t - 75)$$

The solution to this equation is 118.5° F. which is low enough for comfortable handling. The amount of heat absorbing chemical required in this geometry is 91.9 gm., while the canister surface temperature will be 627° F. Note that the canister surface temperature is near enough to the uninsulated case (659° F.) that the reaction rate is not likely to be effected.

In this example, the vapor from the hydrate was vented outside the insulation, so that the thermal properties of the insulation were not changed.

Thus it will be seen that the insulation 25 of this invention actually dissipates heat from the generator cell 12 and does not so isolate the candle 12 against heat radiation as to increase its temperature.

The oxygen generator canister 10 is activated and dispenses oxygen to a mask or cannula by means of a snap-on cap 35 shown in FIGS. 2 to 5. This cap 35 includes a plastic cylindrical body member 36 housing activating mechanism and an outlet tube and a removably cylindrical cover portion 37 housing a face mask and connecting tube. The body member 36 has a cylindrical side wall with an open cylindrical top and a plurality, such as three, flexible fingers 38 extending inwardly from the bottom thereof to snap under the head or rim 21 of the top wall 19 of the tin can 17 and rest on top of the insulation 25. It will be noted from FIG. 5 that these fingers 38 are spaced circumferentially to provide open spaces therebetween venting the tops of the insulation layers to the interior of the body.

The open top of the cylindrical body 36 has a plastics spider 39 with three legs 39a secured therein by screws 40 and projecting thereabove. This spider 39 has a central aperture 41 with a counterbore 42 slidably mounting a circular plastics button 43. A cylindrical insulating ceramics or plastics (phenolic resin) member 44 recessed at its top at 45 and at its bottom at 46 underlies the portion of the spider 39 surrounding the counterbore 42 and a metal plate 47 is mounted under this member 44 and spaced therefrom by spacer sleeves 48. Pins or bolts 49 bottomed on the plate 47, extending through the sleeves 48 and body member 44 and threaded at 50 into the bottom face of the spider 39, assemble the plate 47 and member 44 to the spider.

The plate 47 mounts a central inverted cup 51 with an outturned lip 51a below the plate receiving a silicone rubber sealing ring 52 therearound. This ring 52 is tightly pressed against the end wall 19 around the orifice 22 when the cap is snapped on the bead or ring 21. A metal tube 53 is secured in the side wall of the cup 51 and extends between the plate 47 and member 44 to an insulated rubber tube 54 which extends alongside the member 44 into the cover 37.

The button 43 carries a depending pin 55 extending through the member 44 and cup 51 to an enlarged pointed head 56. A coil spring 57 in the recess 45 of the member 44 surrounds the pin 55 and urges the button 43 against the shoulder 58 between the aperture 41 and the counterbore 42 of the spider 39. In this position, the head 56 depending from the button 43 is bottomed on the top wall of the cup 51 so that its pointed end *56a* will be about flush with the outturned lip 51a of the cup.

When the cap 35 is snapped onto the top of the can 11 with the fingers 38 underlying the bead 21 thereof, the seal ring 52 provides a sealed connection joining the orifice 22 with the interior of the cup 51. Then, when the button 43 is depressed to advance the head 56 through the orifice, the pointed end of the head will pierce the orifice seal 23 and fracture the vial 14 to release water to the ignition cone material, thereby activating the chlorate candle 12 and generating oxygen which will flow through the orifice and cup 51 into the tube 53.

The cover or lid 37 has a mouth portion 59 sized to surround and engage the fingers 39a projecting from the cylindrical body member 36 to be bottomed on the top end of the cylindrical wall 36. This cover member or lid houses a flexible rubber face mask 60 which is anchored at one end 61 to the interior of the cover beyond the mouth portion 59. As shown in FIG. 2, this face mask 60 is folded into the cover 37 when it is assembled on the cap 35 and the insulated tube 54 is also folded into the cap. However, when the cover or lid 37 is removed to a use position as shown in FIG. 3, the face mask 60 is pulled out of the cover 37 so that the tube 54 will feed oxygen from the activated generator to the face mask.

The face mask 60 is a flexible rubber tube which flares outwardly to a very thin end lip portion 62 which can be easily depressed to fit the contours of the face around the mouth and nose of a user. Vent holes 63 are provided around the face mask to relieve excess oxygen and to accommodate exhaling of the user.

The tube 54 may only be insulated at 64 in the area of the metal tube 53 and the insulation can be any desired flexible material. The tube slips over the metal tube 53 at one end and over a nipple 65 projecting from a side wall of the face mask 60.

From the above descriptions it will be understood that disposable oxygen generating canisters 10 of this invention are quickly and easily made available for use by a cap 35 which is easily and quickly mounted on unused canisters and removed from used canisters. The cap is not appreciably heated in use and can be successively used without discomfort. The fingers 38 of the cap are merely snapped over the bead 21 and the cap bottomed on top of the insulation. Then the cover or lid 37 is removed from the cap, the face mask pulled out of the lid, and the button 43 depressed to pierce the canister seal and fracture the water containing vial in the canister for releasing water to activate the ignition material and thereby start the candle to "burn" for releasing oxygen which will flow through the sealed cup 51 and tubes 53 and 54 to the face mask. Vapor released from the hydrate layer 27 between the foil layers 28b and 296 is vented through the cap body 36 and bottom insulation pad 26 so that a user may grasp the sleeve 30 without coming into contact with the hot vapor. The cap 35 acts as a chimney to direct the released water vapor away from the sleeve 30. If the foil layers 28*b* and 29*b* are omitted as shown in FIG. 2-A and the outer peripheral surface or circumference of the assembly is porous, the vapor freely escapes in a radial as well as in an axial direction, and while the surface may become damp it can be comfortably grasped throughout the burning of the oxygen generating candle.

It will also be understood that the heat generated by the "burning" of the candle 12 in the tin can 11 is insulated by the heat dissipating insulation of this invention which by converting sensible heat into heat of vaporization does not raise the temperature in the can and keeps the exterior of the cell at a depressed temperature which is low enough so that the cell can be grasped with bare hands without discomfort.

I claim as my invention:

1. An oxygen generator canister which comprises a metal can having end walls with an orifice in one end wall, an oxygen generating composition housed in said canister which upon ignition undergoes an exothermic reaction with the evolution of oxygen, ignition material in said canister for activating said composition, an inert fibrous blanket containing a means for removing heat wrapped around said can, said heat removing means comprising a water releasing hydrate, said hydrate releasing water when exposed to the heat of reaction of said composition in the canister and forming a vapor which will convert sensible heat into heat of vaporization; and said blanket providing a free and direct passage for radial flow of the vapor to the atmosphere surrounding the blanket whereby the generator canister may be grasped by a user without discomfort from heat generated by the composition.

2. The canister of claim 1 wherein the water releasing hydrate is sandwiched between two inert fibrous blankets.

3. A chemical oxygen generator cell which comprises a disposable metal can having an oxygen outlet at one end thereof and housing a chlorate candle and an ignition material for activating the candle to undergo an exothermic reaction with the evolution of oxygen to said outlet, an inert fibrous insulation blanket surrounding said can and including a means for removing heat, said heat removing means comprising a water releasing hydrate, said hydrate releasing water of hydration at temperatures below about 200°C, and an open ended porous sleeve surrounding said blanket leaving the blanket and hydrate freely exposed both radially and axially to the atmosphere whereby said porous sleeve is adapted to be grasped by a user of the cell without discomfort from heat released during the exothermic reaction.

4. A chemical oxygen generator canister cell having a sealed oxygen outlet means on one end thereof, an oxygen generating chemical in said cell, an open ended tubular body with a passageway means therethrough, said body having means on one end thereof for releasable attachment to the end of the canister cell containing the oxygen outlet means, a cup-shaped lid releasably mounted on the other end of said tubular body, an oxygen mask releasably housed in said cup-shaped lid, said body having an oxygen receiving chamber overlying the oxygen outlet means on said one end of the canister cell to receive oxygen from said outlet means, a tube connecting said chamber with said oxygen mask, means carried by said body for piercing said sealed oxygen outlet means on said one end of the canister cell to activate the oxygen generating chemical in said cell and release oxygen to said chamber for dispensing through said tube to said oxygen mask, and said passageway means through said tubular body providing a chimney for dissipating heat from the canister cell when the lid is removed and the chemical in the canister cell is activated to generate oxygen.

5. An oxygen generator canister which comprises a disposable metal can having an oxygen outlet, a chlorate candle in said can, ignition material in said can for activating the burning of said candle to release oxygen to said outlet, a blanket of low thermal conductivity porous material wrapped around said can, a hydrate in said blanket effective to release water at a temperature below about 200°C to be vaporized by heat from the burning candle to convert sensible heat into heat of vaporization, a porous sleeve surrounding said blanket leaving a free radial flow path for water vapor from the hydrate to the atmosphere through the blanket and sleeve whereby a user of the canister may grasp the sleeve without discomfort caused by excessive heat during oxygen generation.

6. The canister of claim 5 wherein the sleeve is composed of porous material of low thermal conductivity.

7. A chemical oxygen generator which comprises a cylindrical canister having a sealed oxygen outlet, a composition in said canister which upon ignition, generates oxygen and heat, ignition material in said canister for activating said composition, a dispensing cap secured to said canister over said outlet having means for piercing the sealed oxygen outlet and for activating the ignition material and an outlet tube means communicating with the outlet for dispensing oxygen, a face mask carrying cover for said cap, a flexible tube connecting the outlet tube means with the interior of the face mask, and insulation freely and directly exposed to the atmosphere, said insulation surrounding said canister including a cylindrical fibrous blanket means coaxial with the canister, said blanket means containing a means for removing heat, said blanket means being uncovered at its ends and vented to the atmosphere around its cylindrical surface to provide said free and direct exposure to the atmosphere, said heat removing means comprising a water releasing hydrate, said hydrate releasing water which is vaporized when heated by the activated composition in the canister and escapes to the atmosphere through the freely exposed insulation, and said insulation being effective to enable the canister to be grasped by a user without discomfort caused by heat released during oxygen generation.

8. The generator of claim 7 wherein the canister has a bead around one end thereof and the dispensing cap has fingers arranged and constructed to be snapped over said bead to releasably mount the cap on the canister.

9. The generator of claim 7 wherein the insulation includes an inner and an outer blanket with the hydrate sandwiched between the inner and outer blankets and vapor from the hydrate is vented through the dispensing cap.

* * * * *